United States Patent
Stagg et al.

(10) Patent No.: US 10,064,810 B2
(45) Date of Patent: Sep. 4, 2018

(54) MATTE COSMETIC COMPOSITIONS

(71) Applicant: Avon Products, Inc., Suffern, NY (US)

(72) Inventors: Amanda M. Stagg, Morris Plains, NJ (US); Emily H. Rubinson, Suffern, NY (US)

(73) Assignee: Avon Products, Inc., Rye, NY (US)

(*) Notice: Subject to any disclaimer, the term of this patent is extended or adjusted under 35 U.S.C. 154(b) by 0 days.

(21) Appl. No.: 14/718,529

(22) Filed: May 21, 2015

(65) Prior Publication Data

US 2015/0313818 A1 Nov. 5, 2015

Related U.S. Application Data

(63) Continuation-in-part of application No. 14/632,093, filed on Feb. 26, 2015.

(60) Provisional application No. 61/987,291, filed on May 1, 2014.

(51) Int. Cl.

| | | |
|---|---|---|
| *A61Q 1/06* | (2006.01) | |
| *A61K 8/891* | (2006.01) | |
| *A61K 8/37* | (2006.01) | |
| *A61K 8/92* | (2006.01) | |
| *A61K 8/02* | (2006.01) | |
| *A61K 8/25* | (2006.01) | |
| *A61K 8/81* | (2006.01) | |
| *A61K 8/895* | (2006.01) | |

(52) U.S. Cl.
CPC ............. *A61K 8/891* (2013.01); *A61K 8/025* (2013.01); *A61K 8/25* (2013.01); *A61K 8/37* (2013.01); *A61K 8/8111* (2013.01); *A61K 8/895* (2013.01); *A61K 8/92* (2013.01); *A61Q 1/06* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 5,082,660 A | | 1/1992 | Ounanian et al. |
| 5,843,407 A | * | 12/1998 | El-Nokaly ........... A61K 8/0295 252/299.01 |
| 2004/0265348 A1 | * | 12/2004 | Hollenberg .............. A61K 8/11 424/401 |
| 2005/0260148 A1 | | 11/2005 | Elliott et al. |
| 2006/0222606 A1 | | 10/2006 | Elliott et al. |
| 2007/0059263 A1 | | 3/2007 | Taniguchi et al. |
| 2007/0092462 A1 | | 4/2007 | Gans Russ et al. |
| 2008/0152679 A1 | | 6/2008 | Brown |
| 2009/0226498 A1 | | 9/2009 | Flugge-Bernedes et al. |
| 2012/0039831 A1 | | 2/2012 | Musumeci |
| 2012/0263768 A1 | | 10/2012 | Marion |
| 2013/0266797 A1 | | 10/2013 | Teramoto et al. |
| 2013/0295148 A1 | | 11/2013 | Claude-Foly et al. |
| 2015/0313812 A1 | | 11/2015 | Rubinson |

FOREIGN PATENT DOCUMENTS

| | | |
|---|---|---|
| DE | 10064800 A1 | 6/2002 |
| EP | 1640040 A1 | 3/2006 |
| JP | 11-349442 | 12/1999 |
| JP | 11349442 A | 12/1999 |
| JP | 2003/319540 A | 11/2000 |

OTHER PUBLICATIONS

NYX Matte Lipstick, Shocking Prink. (NYX), p. 1, Ingredients, one review on Oct. 30, 2012 http://www.amazon.com/NYX-Matte-Lipstick-Shocking-Pink/dp/B005FYJBFG/ref=sr 1_1_a_it?ie=UTF8 &qid=1462399986&sr=8-1&keywords+matt+lipstick+nyx.
Kobo Products, Inc., Microspheres. Technical Literature ref MSp-004. 2012.
Floratech, Emollients Formulation Guide. 2007.
The Innovative Company, Novatext Velvet.
MicroPowder, Micropoly, (2008).
MicroPowder, Microsorb 994s, (2013).

* cited by examiner

*Primary Examiner* — Jennifer A Berrios
(74) *Attorney, Agent, or Firm* — Brian P. McCloskey

(57) ABSTRACT

The present invention relates generally to cosmetic compositions that impart a matte finish to human integuments. More specifically, the invention relates to lip cosmetics that impart a matte finish.

16 Claims, No Drawings

MATTE COSMETIC COMPOSITIONS

CROSS-REFERENCE TO RELATED APPLICATIONS

This application is a continuation in part of U.S. patent application Ser. No. 14/632,093, filed on Feb. 26, 2015, which claims priority to U.S. Provisional Patent Application Ser. No. 61/987,291, filed on May 1, 2014, the entire contents of each being incorporated by reference herein for all purposes.

FIELD OF INVENTION

The present invention relates generally to cosmetic compositions that impart a matte finish to human integuments. More specifically, the invention relates to lip cosmetics that impart a matte finish to the lips.

BACKGROUND

Many cosmetics such as lipsticks, foundations, and powders, are designed to impart a matte finish to the lips or skin. Cosmetics with a glossy finish tend to highlight fine lines and wrinkles, whereas a matte finish softens the look of such imperfections. In addition, an oily or shiny appearance of the skin is considered by many to be undesirable.

Conventionally, matte cosmetics rely on a low emollient content to reduce gloss and shine and create a matte finish. Other matte cosmetics use high levels of mattifying powders, such as mica, talc, and the like. These reduced emollient formulations are often viewed by consumers as drying and uncomfortable.

There is therefore a need for cosmetic compositions, such as lipstick compositions, that provide a matte finish, without compromising comfort. It is therefore an object of the present invention to provide cosmetic compositions, including color cosmetics, such as lipsticks, which achieve low gloss and comfortable wear attributes.

SUMMARY OF THE INVENTION

In accordance with the foregoing objectives and others, the present invention provides cosmetic compositions (e.g., color cosmetics such as lipstick) characterized by a non-shiny, matte finish (e.g., having a gloss value of less than about 20, or less than about 15, or less than about 10, or less than about 8, or less than about 6 gloss units) when drawn down into films. The cosmetic compositions of the invention ideally possess desirable wear properties, such as comfort, not having a "heavy" feel on the lips, and not being drying like other matte cosmetics which rely on low emollient levels (e.g., <10%) and/or high content (e.g., >15%) of mattifying powder (e.g., silica, mica, etc.).

It has been discovered that low gloss cosmetic compositions, such as lipsticks, can be formulated with high (e.g., >10%, >12.5%, >15%, etc.) levels of certain ester oils, including ethylhexyl palmitate, which surprisingly do not impair the matte finish to the degree seen with ester oils commonly found in lipsticks, while also providing excellent emolliency. In one aspect of the invention, compositions, notably lipsticks, are provided comprising ethylhexyl palmitate in an amount from about 10% to about 30% (e.g., between about 10-15%, or between about 15-20%, or between about 20-25%) or between about 25-30% by weight of the composition, effective to impart a matte finish to the lips without a heavy, drying feeling on the lips. The matte lipstick may comprise one or more additional ester oils, such as isopropyl isostearate, capable of imparting emolliency. Such additional ester oils may be present in an amount, individually or collectively, from about 0.1-30% by weight, more typically from about 1% to about 25% (e.g., between about 5-10%, or between about 10-15%, or between about 15-20%, or between about 20-25%) by weight of the composition. In some implementations, the amount of ethylhexyl palmitate is greater than the amount of all other ester oils, alone or in combination, in the composition. In some embodiments, the amount of ethylhexyl palmitate is greater than the amount of all other emollients in the composition. In some embodiments, the amount of ethylhexyl palmitate is greater than the amount of all non-volatile silicone oil emollients in the composition. In other embodiments, the amount of ethylhexyl palmitate is greater than the amount of all non-volatile hydrocarbon oil emollients in the composition. In some embodiments, a matte cosmetic, such as a lipstick, may comprise ethylhexyl palmitate and isopropyl isostearate. In some embodiments, the weight ratio of ethylhexyl palmitate to a second ester oil, such as a mono-ester (e.g., isopropyl isostearate) will be from about 4:1 to about 1:4, or from about 3:1 to about 1:3, or from about 2:1 to about 1:2. The combination of ethylhexyl palmitate and isopropyl isostearate in a lipstick has been found to provide unexpected or synergistic reduction in gloss value compared to otherwise identical lipsticks lacking either isopropyl isostearate or ethylhexyl palmitate. In some embodiments, the matte lipstick may comprise a total emollient content (e.g., non-volatile dimethicone; silicone crosspolymers; hydrocarbon oils such as mineral oil, petrolatum, polyolefins, etc.; ester oils, including without limitation, ethylhexyl palmitate, isopropyl isostearate, octyl isononanoate, polyglycerol diisostearate, etc.) in an amount between about 30% and about 60% (e.g., about 30-40%, or about 40-45%, or about 45-50%, or about 50-55%, or about 55-60% by weight of the composition. The matte lipstick may also comprise one or more waxes (e.g., paraffin wax, ozokerite wax, carnauba wax, microcrystalline wax, etc.) in an amount, individually or collectively, between about 5% and about 20% (e.g., about 5-10%, or about 10-12.5%, or about 12.5-15%, or about 15-20%) by weight of the composition. In some embodiments, the amount of carnauba wax, if present, is less than 1%, or less than 0.75%, or less than 0.5% by weight of the compositions. In some embodiments, the compositions are free of carnauba wax. In some implementations, the total amount of ethylhexyl palmitate is greater than the sum of all waxes present in the composition. The matte lipstick may also comprise a silicone crosspolymer (e.g, Dimethicone Crosspolymer), for example, in an amount between about 1% and about 10% (e.g., about 1-2%, or about 2-4%, or about 4-6%, or about 6-8%, or about 8-10%) by weight of the composition. The matte lipstick may also comprise one or more of spherical silica, hydrous calcium silicate, and polyethylene powder in an amount, individually or collectively, between about 1% and about 10% (e.g., about 1-2%, or about 2-3%, or about 3-4%, or about 4-5%, about 5-6%, about 6-7%, about 7-8%, about 8-9%, or about 9-10%) by weight of the composition. The compositions may further comprise a colorant (e.g., pigments, lakes, dyes, etc.), sunscreens, film formers, thickeners, humectants, and other cosmetic adjuvants in individual or collective amount from about 0.001% to about 35% by weight, provided that such ingredients are not included in amounts incompatible with achieving the desired matte finish. The compositions may be aqueous, substantially anhydrous (e.g., less than 2% water), or anhydrous. The compositions may also be substantially free of shine agents (e.g., polybutene, hydrogenated polyisobutene, amodimethicone, phenlytrimethicone, and emollients having a refractive index of 1.47 or more, including esters and other emollients with refractive indices of 1.49 or more, 1.5 or more, or 1.52 or more). The cosmetic lip composition is adapted for application to the lips to form a matte film thereon. In one aspect of the invention, a method is provided for imparting matter color to a human integument (e.g., the lips) comprising applying a film of a matte composition of the invention to the lips.

These and other aspects of the present invention will become apparent to those skilled in the art after a reading of the following detailed description of the invention, including the appended claims.

DETAILED DESCRIPTION

All terms used herein are intended to have their ordinary meaning unless otherwise provided. All ingredient amounts provided herein are by weight percent of the total composition unless otherwise indicated. It will be understood that the total of all weight percentages and the total volume percentages in a given composition will not exceed 100%. If the amounts of a particular component are not otherwise specified, all components of the compositions of the invention may be present in amounts from about 0.0001% to about 99% by weight, including amounts from about 0.001% to about 50% by weight, or from about 0.01% to about 25% by weight, or from about 0.1% to about 10% by weight.

The term "consisting essentially of" is intended to include only those components that do not materially alter the basic and novel features of the inventive compositions, including without limitation, the low gloss of the composition and/or wear properties (e.g., comfort).

The term "mattifying particulates," as used herein, refers to particulates characterized by an ability to absorb substantial amounts of oil. In some embodiments, mattifying particulates and pigments are capable (individually or based on combinations of different particulates or pigments) of absorbing at least 40 g/100 g, or at least 50 g/100 g, or at least 60 g/100 g, or at 70 g/100 g of oil as determined by ASTM D281-12.

The term "mattifying polymeric powder," as used herein, refers to a polymeric powder having an oil absorption value greater than 70 g/100 g as determined by ASTM D281-12. Mattifying polymeric powders (e.g., mattifying polyethylene powder) may have an oil absorption value greater than 80, greater than 90, greater than 100, greater than 110, greater than 120, greater than 130, greater than 140, greater than 150, greater than 160, greater than 170, greater than 180, greater than 190, or greater than 200 g/100 g.

The present invention is based in part on the discovery that low gloss cosmetic compositions, such as lipsticks, can be formulated with high levels of certain ester oils which surprisingly do not impair the matte appearance to the degree observed with other ester oils commonly found in cosmetics such as lipsticks, while also providing excellent emolliency. The compositions of the invention are characterized by a non-shiny, matte finish, and in some embodiments will have a gloss value of less than about 20, or less than about 15, or less than about 10, or less than about 8, or less than about 6 gloss units when drawn down into films. The compositions ideally possess desirable wear properties, such as comfort, not having a "heavy" feel on the lips, and not being perceived as drying like conventional matte cosmetics which rely on low emollient levels (e.g., <10%) and/or high (e.g., >15%) mattifying powder (e.g., silica, mica, etc.) content.

In some embodiments, the compositions comprise ethylhexyl palmitate in an amount from about 10% to about 40%, or from about 10% to about 30%, or from about 12.5% to about 25%, or from about 15% to about 20% by weight of the composition. The comfort and wear properties can be determined using consumer panel testing.

The compositions may further comprise one or more additional ester oils. The additional esters may be, for example, mono-esters, di-esters, or tri-esters. Ideally, the additional esters, if present, also provide emolliency to the composition. In some embodiments, one or more additional esters oils is present in an amount, individually or collectively, from about 5% to about 25%, or from about 5% to about 10%, or from about 10% to about 15%, or from about 15% to about 20%, or from about 20% to about 25% by weight of the composition. In some embodiments, the amount of ethylhexyl palmitate is present in the composition in an amount greater than the amount of all other ester oils, individually or in the aggregate, in the composition.

Other suitable additional ester oils that may used in the compositions of the invention include fatty acid esters, and in particular, those esters commonly used as emollients in cosmetic formulations. Such esters will typically be the esterification product of an acid of the form $R_4(COOH)_{1-2}$ with an alcohol of the form $R_5(OH)_{1-3}$ where $R_4$ and $R_5$ are each independently linear, branched, or cyclic hydrocarbon groups, optionally containing unsaturated bonds (e.g., from 1-6 or 1-3 or 1), and having from 1 to 30 (e.g., 6-30 or 8-30, or 12-30, or 16-30) carbon atoms, optionally substituted with one or more functionalities including hydroxyl, oxa, oxo, and the like. Preferably, at least one of $R_4$ and $R_5$ comprises at least 8, or at least 10, or at least 12, or at least 16 or at least 18 carbon atoms, such that the ester oil comprises at least one fatty chain. The esters defined above will include, without limitation, the esters of mono-acids with mono-alcohols, mono-acids with diols and triols, di-acids with mono-alcohols, and tri-acids with mono-alcohols.

Suitable fatty acid esters include, without limitation, butyl isostearate, butyl oleate, butyl octyl oleate, cetyl palmitate, ceyl octanoate, cetyl laurate, cetyl lactate, cetyl isononanoate, cetyl stearate, diisostearyl fumarate, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl isononate, isohexyl neopentanoate, isohexadecyl stearate, isopropyl isostearate, n-propyl myristate, isopropyl myristate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-$C_{12-13}$-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyldodecyl myristate or lactate, di(2-ethylhexyl)succinate, tocopheryl acetate, and the like.

Other suitable esters include those wherein $R_5$ comprises a polyglycol of the form H—(O—CHR*—CHR*)$_n$— wherein R* is independently selected from hydrogen or straight chain $C_{1-12}$ alkyl, including methyl and ethyl, as exemplified by polyethylene glycol monolaurate.

Salicylates and benzoates are also contemplated to be useful esters in the compositions of the invention. Suitable salicylates and benzoates include esters of salicylic acid or benzoic acid with an alcohol of the form $R_6$OH where $R_6$ is a linear, branched, or cyclic hydrocarbon group, optionally containing unsaturated bonds (e.g., one, two, or three unsaturated bonds), and having from 1 to 30 carbon atoms, typically from 6 to 22 carbon atoms, and more typically from 12 to 15 carbon atoms. Suitable salicylates include, for example, octyl salicylate and hexyldodecyl salicylate, and benzoate esters including $C_{12-15}$ alkyl benzoate, isostearyl benzoate, hexyldecyl benzoate, benzyl benzoate, and the like.

Other suitable esters include, without limitation, polyglyceryl diisostearate/IPDI copolymer, triisostearoyl polyglyceryl-3 dimer dilinoleate, polyglycerol esters of fatty acids, and lanolin, to name but a few.

In one embodiment, the compositions comprise ethylhexyl palmitate and isopropyl isostearate. In some embodiments, the combination of ethylhexyl palmitate and isopropyl isostearate in a composition has been found to provide unexpected or synergistic reduction in gloss value compared to otherwise identical compositions lacking either isopropyl isostearate or ethylhexyl palmitate. In some embodiments, the gloss value of a composition comprising ethylhexyl palmitate and isopropyl isostearate is less than about 10, or less than about 9, or less than about 8, or less than about 7, or less than about 6 gloss units. In one embodiment, the composition comprises ethylhexyl palmitate in an amount from about 10% to about 25%, or from about 15% to about 20% by weight of the composition and isopropyl isostearate in an amount from about 5% to about 15%, or from about 8% to about 12% by weight of the composition.

In one embodiment, the weight ratio of ethylhexyl palmitate to a second ester oil, such as, without limitation, isopropyl isostearate, is from about 5:1 to about 1:5, or from about 4:1 to about 1:4, or from about 3:1 to about 1:3, or from about 2:1 to about 1:2.

In one embodiment, a matte lipstick is provided comprising: (1) from about 30-40% by weight of ethylhexyl palmitate in combination with an ester oil; the weight ratio of said ethylhexyl palmitate to said ester oil being from about 3:1 to about 1:3; and (2) from about 10-30% by weight of non-volatile dimethicone and a silicone crosspolymer; the weight ratio of said dimethicone to said silicone crosspolymer being from about 10:1 to about 1:10.

In some embodiments, the compositions comprise ethyhexyl palmitate and octyl isononanoate.

In some embodiments, the composition may comprise a total emollient content in an amount from about 30-70% by weight, including, for example, from 30% to about 35%, or from about 35% to about 40%, or from about 40% to about 45%, or from about 45% to about 50%, or from about 50% to about 55%, or from about 55% to about 60%, or from about 60% to about 65%, or from about 65% to about 70% by weight of the composition. Suitable emollients include, without limitation, ester oils, and any of the emollient oils described herein. In some embodiments, the amount of ethylhexyl palmitate is present in the composition in an amount greater than the amount of all non-volatile silicone oils in the composition. In other embodiments, the amount of ethylhexyl palmitate is present in the composition in an amount greater than the amount of all non-volatile hydrocarbon oils in the composition.

Suitable emollient oils include, for example, non-volatile silicone-containing oils, and in particular, silicone elastomers and/or silicone crosspolymers. Examples include Dimethicone Crosspolymer (INCI), Dimethicone/Vinyl Dimethicone Crosspolymer (INCI), Cetearyl Dimethicone Crosspolymer (INCI), C30-45 Alkyl Cetearyl Dimethicone Crosspolymer (INCI), Acrylates/Dimethicone Copolymer (INCI), Dimethicone Copolymer (INCI), Vinyl Dimethicone/Methicone Silsesquioxane Crosspolymer (INCI), and Polysilicone-11 (INCI), to name a few. In one embodiment, the low gloss emollient comprises Dimethicone Crosspolymer (INCI). The Dimethicone Crosspolymer may be dissolved or dispersed in a solvent such as dimethicone. The solvent for the Dimethicone Crosspolymer (or other silicone emollient) may have a flash point above 125° F., or above 150° F. or above 175° F. or above 200° F. Particular mention may be made of the product sold by Dow Corning under the name 9041 Silicone Elastomer Blend, which comprises Dimethicone Crosspolymer in 5 centistoke Dimethicone and has a flash point above 215° F. Each of the foregoing silicone-based polymers may be used in combination with one another or in combination with other polymers, including polyolefins, acrylates, and the like.

In one embodiment, the low gloss emollient typically has a gloss value (individually or in the aggregate) less than the gloss value of castor oil. The low gloss oil may comprise any of the oils and/or emollient oils described herein, individually or in combination. In one embodiment, the low gloss oil comprises one or more of ester oils, hydrocarbon oils, silicon-containing oils, and organic fatty alcohols. As used herein, the term emollient is intended to refer to oils that provide a softening, smoothing and/or moisturizing effect to the skin.

In one embodiment, a low gloss emollient may comprise the material having the INCI name Hydrogenated Polyisobutene (and) Polymethylsilsesquioxane (and) Vinyl Dimethicone/Methicone Silsesquioxane Crosspolymer (and) Ethylene/Propylene Copolymer (available from Innovations Company as Novatext® MAT). The low gloss emollient may comprise hydrogenated polyisobutene in an amount from about 60% to about 80% by weight, polymethylsilsesquioxane in an amount from about 5% to about 15% by weight, vinyl dimethicone/methicone silsesquioxane crosspolymer in an amount between 5% to about 15% by weight, and ethylene/propylene copolymer in an amount between about 1% and about 10% by weight.

The low gloss emollient may comprise a silicone elastomer and/or a silicone crosspolymer. In one embodiment, the emollient comprises Dimethicone Crosspolymer (INCI). The silicone crosspolymer may be present in an amount from about 1% to about 10% by weight of the composition. For example, the silicone crosspolymer may be present in an amount of about 2%, or about 4%, or about 6%, or about 8% by weight of the composition. In one embodiment, the low gloss emollient comprises Hydrogenated Polyisobutene (and) Polymethylsilsesquioxane (and) Vinyl Dimethicone/Methicone Silseaquioxane Crosspolymer (and) Ethylene/Propylene Copolymer (INCI).

The oil may also comprise a volatile or non-volatile silicone oil. Suitable silicone oils include linear or cyclic silicones such as polyalkyl- or polyarylsiloxanes, for example, comprising alkyl groups having from 1 to 16 carbon atoms. Representative silicone oils include, for example, caprylyl methicone, stearyl dimethicone, cyclomethicone, cyclopentasiloxane decamethylcyclopentasiloxane, decamethyltetrasiloxane, diphenyl dimethicone, dodecamethylcyclohexasiloxane, dodecamethylpentasiloxane, heptamethylhexyltrisiloxane, heptamethyloctyltrisiloxane, hexamethyldisiloxane, methicone, methyl-phenyl polysiloxane, octamethylcyclotetrasiloxane, octamethyltrisiloxane, perfluorononyl dimethicone, polydimethylsiloxanes, amodimethicone, dimethiconol, dimethicone copolyol, and combinations thereof. The silicone oil will typically, but not necessarily, have a viscosity of between about 5 and about 3,000 centistokes (cSt), preferably between 50 and 1,000 cSt measured at 25° C.

In one embodiment, the silicone oil may be a fluorinated silicone, such as a perfluorinated silicone (i.e., fluorosilicones). Fluorosilicones are advantageously both hydrophobic and oleophobic and thus contribute to a desirable slip and feel of the product. Fluorosilicones can be gelled with behenyl behenate if desired. One suitable fluorosilicone is a fluorinated organofunctional silicone fluid having the INCI name Perfluorononyl Dimethicone. Perfluorononyl Dimethicone is commercially available from Phoenix Chemical under the trade name PECOSIL®.

The compositions may also comprise hydrocarbon oils. Exemplary hydrocarbon oils comprise straight or branched chain paraffinic hydrocarbons having from 5 to 80 carbon atoms, typically from 8 to 40 carbon atoms, and more typically from 10 to 16 carbon atoms, including but not limited to, pentane, hexane, heptane, octane, nonane, decane, undecane, dodecane, tetradecane, tridecane, and the like. Some useful hydrocarbon oils are highly branched aliphatic hydrocarbons, including $C_{8-9}$ isoparaffins, $C_{9-11}$ isoparaffins, $C_{12}$ isoparaffin, $C_{20-40}$ isoparaffins and the like. Special mention may be made of the isoparaffins having the INCI names isohexadecane, isoeicosane, and isododecane (IDD).

Also suitable as hydrocarbon oils are poly-alpha-olefins, typically having greater than 20 carbon atoms, including (optionally hydrogenated) $C_{24-28}$ olefins, $C_{30-45}$ olefins, polyisobutene, hydrogenated polyisobutene, hydrogenated polydecene, polybutene, hydrogenated polycyclopentane, mineral oil, pentahydrosqualene, squalene, squalane, and the like. The hydrocarbon oil may also comprise higher fatty alcohols, such as oleyl alcohol, octyldodecanol, and the like.

Additional suitable oils may include, for example, isostearyl neopentanoate, isostearyl stearate, castor oil, lauryl lactate, isopropyl palmitate, glyceryl triacethyl hydroxystearate, diisopropyl adipate, octyl isononanoate, neopentyl glycol dioctanoate, neopentyl glycol dicaprate, isodecyl oleate, and myristyl myristate.

Other suitable oils include, without limitation, castor oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, avocado oil, camellia oil, macadamia nut oil, turtle oil, mink oil, soybean oil, grape seed oil, sesame oil, maize oil, rapeseed oil, sunflower oil, cottonseed oil, jojoba oil, peanut oil, olive oil, and combinations thereof.

In one embodiment, the composition comprises from about 0.1-20%, or from about 0.5-15%, or from about 1-10%, or from about 2.5-7.5%, or from about 3-5% by weight lanolin.

The compositions may comprise one or more waxes in an amount, individually or collectively, from about 5% to about 20%, or from about 15% to about 20%, or from about 10% to about 12.5%, or about 12.5% or about 15% by weight of the composition. In some embodiments, the total amount of ester oils is greater than the sum of all waxes present in the composition. In some embodiments, the amount of carnauba wax is present in an amount of less than 1%, or less than 0.75%, or less than 0.5% by weight of the composition. In some embodiments, the composition is free of carnauba wax.

Any suitable waxes may be used in the compositions of the invention, and may comprise natural, mineral and/or synthetic waxes. Natural waxes include those of animal origin (e.g., beeswax, spermaceti, lanolin, and shellac wax) and those of vegetable origin (e.g., carnauba, candelilla, bayberry, and sugarcane wax). Mineral waxes include, without limitation microcrystalline, ozokerite, ceresin, montan, paraffin, petroleum, and petrolatum waxes. Synthetic waxes include, for example, polyethylene glycols such as PEG-18, PEG-20, PEG-32, PEG-75, PEG-90, PEG-100, and PEG-180 which are sold under the tradename CARBOWAX® (The Dow Chemical Company). Mention may be made of the polyethylene glycol wax CARBOWAX 1000 which has a molecular weight range of 950 to 1,050 and a melting point of about 38° C., CARBOWAX 1450 which has a molecular weight range of about 1,305 to 1,595 and a melting point of about 56° C., CARBOWAX 3350 which has a molecular weight range of 3,015 to 3,685 and a melting point of about 56° C., and CARBOWAX 8000 which has a molecular weight range of 7,000 to 9,000 and a melting point of about 61° C.

Suitable synthetic waxes also comprise Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated) with melting points ranging from 80° C. to 132° C. Commercially available ethylene-α-olefin copolymer waxes include, for example, those sold under the tradename PETROLITE® Copolymers (Baker Hughes Incorporated) with melting points ranging from 95° C. to 115° C.

Other suitable waxes include silicone waxes, including alkyl silicones, such as alkyl dimethicone and alkyl methicone waxes.

The compositions may also comprise a mattifying polymeric powder, such as a mattifying polyethylene (PE) powder, which is typically micronized. The polymeric powder will typically comprise an organic polymer, and more typically a polyolefin polymer (e.g., a polyolefin homopolymer or copolymer) comprising the polymerization product of at least one unsaturated monomer selected from ethylene, propylene, butylene, styrene, tetrafluoroethylene, (alkyl) acrylate, vinyl alcohol, vinyl pyrrolidone, and combinations thereof. In other embodiments, the polymeric powder may comprise a polyamide polymer, a polyurethane polymer, a silicone polymer, and a polyester polymer. Such a powder may be distinguished from traditional polymeric powders (e.g., PE powders) in that the mattifying polymeric powders of the invention are treated to increase the matte properties. For example, the mattifying polymeric powder (e.g., PE) may be treated with a material such as silica and/or a silicate. The material may be in particulate form and may be bonded or adhered to the surface of the PE particles. The treatment material may include a soft focus material such as spherical silica. The mattifying powder may, in some embodiments, comprise Polyethylene (and) Calcium Silicate (and) Silica (INCI).

The mattifying powder may be used in combination (e.g., synergistic combination) with a low gloss oil or emollient. The low gloss oil or emollient typically has a gloss value less than castor oil. In some embodiments, the low gloss oil will have a refractive index of less than 1.5, or less than 1.48, or less than 1.46, or less than 1.44, or less than 1.42, or less than 1.4, or less than 1.38 at 25° C. In some embodiments, individual oils and emollients will have the foregoing refractive indices. In other embodiments, all oil and/or emollients will collectively have the foregoing refractive indices.

In some embodiments, the mattifying polymeric powder comprises a mattifying PE powder. Special mention may be made of the material having the INCI name Polyethylene (and) Calcium Silicate (and) Silica (available as Microsorb 944S, from MicroPowders, Inc.). In one embodiment, the mattifying PE powder is the product of co-extrusion of powdered PE, calcium silicate, and silica (e.g., spherical silica). It is believed that the polyethylene is coated by the calcium silicate and/or silica. The particle size of the mattifying powder may be, for example, from about 5 to about 100 μm, or from about 10 to about 75 μm, or from about 25 to about 35 μm. The mattifying powder may comprise polyethylene powder in an amount from about 50% to about 70% by weight, optionally calcium silicate in an amount from about 30% to about 50% by weight, and optionally, silica (e.g., spherical silica) in an amount from about 0.5% to about 5% by weight.

The mattifying polymeric powder, when present, is typically present in an amount effective to impart a matte appearance, and in particular, a gloss of less than 60 gloss units. In some embodiments, the mattifying powder comprises from about 0.1 to about 35% by weight, or from about 0.5% to about 20% by weight, or from about 1% to about 15% by weight, or from about 1.5% to about 10% by weight, or from about 2% to about 5% by weight of the composition. In other embodiments, the mattifying powder comprises about 0.5%, 1%, or about 2%, or about 3%, or about 4%, or about 5% by weight of the composition.

In some embodiments, the mattifying polymeric powder has a higher oil absorbency by ASTM D281-12 compared to talc (e.g., untreated talc powder) having a median particle size from about 0.5-50 μm or from about 1-10 μm or from about 3-4 μm or about 32 μm. In some embodiments, the mattifying polymeric powder has a higher oil absorbency compared to mica. In some embodiments, the mattifying polymeric powder has an oil absorbency of between 100-200 g/100 g.

When present, the combination of mattifying powder and emollient in the compositions of the invention may allow for a lower total mattifying particulate content than that of traditional matte finish cosmetics, while achieving a desirable, low gloss value. Mattifying particulates may include, without limitation, polymeric powders (e.g, micronized polyethylene that is not treated with silica and/or silicates), fillers, talc, etc. The compositions may comprise a total mattifying particulate content of less than about 40%, or less than about 35%, or less than about 30%, or less than about 25%, or less than about 20%, or less than about 15%, or less than about 10% by weight, or less than about 5% by weight of the composition.

In one embodiment, the composition may comprise one or more of spherical silica, calcium silicate, and polyethylene powder in an amount, individually or collectively, between about 1% and about 10% (e.g., about 2%, or about 3%, or about 4%, or about 5%, about 6%, about 7%, about 8%, about 9%) by weight of the composition.

In some embodiments, the total particulate content of the compositions (e.g., including mattifying powder, pigments, fillers, and all other particulates) will be less than the levels typically associated with conventional matte appearance cosmetics that are characterized by a gloss value of less than 40. The total particulate content in some embodiments may be less than about 40%, or less than about 35%, or less than about 30%, or less than about 25%, or less than about 20%, or less than about 15%, or less than about 10% by weight of the composition.

In some embodiments, the total particulate content of the composition has an aggregate oil absorption by ASTM D281-12 of greater than 10 g/100 g, greater than 15 g/10 g, greater than 20 g/100 g, greater than 25 g/100 g, greater than 30 g/100 g, greater than 35 g/100 g, greater than 40 g/100 g, greater than 45 g/100 g, greater than 50 g/100 g, greater than 55 g/100 g, greater than 60 g/100 g, greater than 65 g/100 g, greater than 70 g/100 g, or greater than 75 g/100 g. In some embodiments, the oil absorbency of the total combined particulates is greater than the oil absorbency of talc.

In some embodiments, the compositions are free of or are "substantially free" of mica, pearls and interference pigments by which is meant that the composition contains less than 5% by weight of such materials individually or in the aggregate. In some embodiments, the composition comprises less than about 2.5%, less than about 1%, less than about 0.5%, or less than about 0.1% of such materials.

In some embodiments, the compositions may comprise the combination of (i) micronized polyethylene and (ii) Polyethylene (and) Calcium Silicate (and) Silica (INCI), in an amount less than about 20%, less than about 15%, less than about 10%, or less than about 5% by weight of the composition. In some embodiments, the oil absorbency of (ii) is greater than the oil absorbency of (i). In some embodiments, a low gloss emollient (e.g., Dimethicone Crosspolymer) is included in an amount from about 5-30% by weight.

The compositions may be substantially anhydrous. "Substantially anhydrous" as used herein means containing less than 5% by weight water. In other embodiments, the compositions will comprise less than about 2.5%, or less than about 2%, or less than about 1% by weight water, or less than 0.25% by weight water. In some embodiments, the compositions may be anhydrous. The term "anhydrous" as used herein means that no water is added to the composition and that only that amount of moisture absorbed from the atmosphere will be present in the composition.

The compositions may be "substantially free" of agents that provide or enhance shine ("shine agents"), by which is meant that the amount of any such shine agents increase the gloss, if at all, by less than 3, 2, or 1 gloss unit. In some embodiments, gloss agents will comprise less than 5% by weight less than about 2.5%, or less than about 1%, or less than about 0.5%, or less than about 0.1% by weight of the composition. In some embodiments, the compositions of the invention are free of shine agents.

Shine agents may include materials having a refractive index greater than 1.4, or greater than 1.45, or greater than 1.47, or greater than 1.49, or greater than 1.5, or greater than 1.52 when measured as a film at 25° C. In some embodiments, the compositions of the invention are substantially free of or are free of one or more of the following: amodimethicone, phenyltrimethicone, polyols (e.g., glycerin), fatty esters having a gloss value greater than castor oil, silicone phenylpropyldimethylsiloxysilicate, polybutene, polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In some embodiments, the term "shine agent" does not include organic sunscreens.

In some embodiments, the compositions may be free of, or substantially free of glycerin and/or silicone-containing solvents, oils, and/or film forming polymers, by which is meant that the composition comprises less than 5% by weight of either or both. "Substantially free" as used herein means containing less than 5% by weight. In some embodiments, the compositions comprise less than about 2.5% or less than about 1.5%, or less than about 1.5%, or less than 1%, or less than 0.5%, or less than 0.1% by weight glycerin and/or silicone containing solvents, oils, and/or film-forming polymers. In some embodiments, the compositions are substantially free of volatile solvents, including volatile silicone solvents having a flash point below 200° F., or below 175° F., or below 150° F., or below 120° F., or below 100° F.

A composition may be assessed for shine/gloss intensity using a gloss meter, which measures the gloss intensity, or shine, of a cosmetic film and provides gloss values in "gloss units." The compositions of the invention are typically characterized by a matte finish, by which is meant that the composition has a gloss value of less than about 60, or less than about 50, or less than about 40, or less than about 30, or less than about 20, or less than about 15, or less than about 10, or less than about 5, or less than about 4, or less than about 3, or less than about 2 gloss units.

The compositions of the invention may also comprise colorants, such as pigments, dyes, and lakes. In one embodiment, the compositions comprise a pigment, such as iron oxide and/or carbon black. Additional suitable pigments include inorganic pigments include, including, not limited to, inorganic oxides and hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO) and iron hydroxides including red iron oxide, yellow iron oxide and black iron oxide, titanium dioxide, titanium lower oxides, zirconium oxides, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. In some embodiments, the inorganic oxide particles may be selected from silica, alumina, zinc oxide, iron oxide and titanium dioxide particles, and mixtures thereof. In one embodiment, the pigments have a particle size from 5 nm to 100 microns, or from 5 nm to 25 microns, or from 10 nm to 10 microns. In some embodiments, the particle size (median) will be less than bout 5 microns or less than 1 micron.

Additional exemplary color additive lakes include, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI# 16035); FD&C Blue #1 (CI# 42090); FD&C Yellow #5 (CI# 19140); or any combinations thereof.

The pigments may be optionally surface treated, for example, to make the particles more hydrophobic or more dispersible in a vehicle. The surface of the particles may, for example, be covalently or ionically bound to an organic molecule or silicon-based molecule or may be absorbed thereto, or the particle may be physically coated with a layer of material. The surface treatment compound may be attached to the particle through any suitable coupling agent, linker group, or functional group (e.g., silane, ester, ether, etc). The compound may comprise a hydrophobic portion which may be selected from, for example, alkyl, aryl, allyl, vinyl, alkyl-aryl, aryl-alkyl, organosilicone, di-organosilicone, dimethicones, methicones, polyurethanes, silicone-polyurethanes, and fluoro- or perfluoro-derivatives thereof. Other hydrophobic modifiers include, but are not limited, lauroyl lysine, Isopropyl Titanium Triisostearate (ITT), ITT and Dimethicone (ITT/Dimethicone) cross-polymers, ITT and Amino Acid, ITT/Triethoxycaprylylsilane Crosspolymer, waxes (e.g., carnauba), fatty acids (e.g., stearates), HDI/Trimethylol Hexylactone Crosspolymer, PEG-8 Methyl. Ether Triethoxysilane, aloe, jojoba ester, lecithin, perfluoroalcohol phosphate, and Magnesium Myristate (MM). In other embodiments, the pigments may be surface treated with galactoarabinose or glyceryl rosinate. In another embodiment, the pigments may be surface treated with Disodium Stearoyl Glutamate (and) Aluminum Dimyristate (and) Triethoxycaprylysilane.

Various fillers and additional components may be added to the compositions. Fillers may be present in an amount between about 0.1% and about 20% by weight of the composition, more typically between about 0.1% and about 10% by weight of the composition. Suitable fillers include, without limitation, silica, treated silica, talc, zinc stearate, mica, kaolin, Nylon powders such as Orgasol®, polyethylene powder, PTFE (e.g., Teflon®), powders, polypropylene powder, acrylates powders, starch, boron nitride, copolymer microspheres such as Expancel® (Nobel Industries), Polytrap® (Dow Corning) and silicone resin microbeads (Tospearl® from Toshiba), and the like.

Other fillers that may be used in the compositions of the invention include inorganic powders such as chalk, fumed silica, fumed alumina, calcium oxide, calcium carbonate, magnesium oxide, magnesium carbonate, Fuller's earth, attapulgite, bentonite, muscovite, phlogopite, synthetic mica, lepidolite, hectorite, biotite, lithia mica, vermiculite, aluminum silicate, aluminum magnesium silicate, diatomaceous earth, starch, alkyl and/or trialkyl aryl ammonium smectites, chemically modified magnesium aluminum silicate, organically modified montmorillonite clay, hydrated aluminum silicate, hydrated silica, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicon dioxide; organic powder, cyclodextrin, methyl polymethacrylate powder, copolymer powder of styrene and acrylic acid, benzoguanamine resin powder, and poly(ethylene tetrafluoride) powder.

The compositions of the invention may comprise a film former, and in particular, a polymeric film former. The term polymeric film former may be understood to indicate a polymer which is capable, by itself or in the presence of at least one auxiliary film-forming agent, of forming a continuous film which adheres to a surface and functions as a binder for the particulate material. Suitable polymeric film formers include, without limitation, acrylic polymers or co-polymers, (meth)acrylates, alkyl (meth)acrylates, polyolefins, polyvinyls, polacrylates, polyurethanes, silicones, polyamides, polyethers, polyesters, fluoropolymers, polyethers, polyacetates, polycarbonates, polyamides, polyimides, rubbers, epoxies, formaldehyde resins, organosiloxanes, dimethicones, amodimethicones, dimethiconols, methicones, silicone acrylates, polyurethane silicones copolymers, cellulosics, polysaccharides, polyquaterniums, and the like. Suitable film formers include those listed in the Cosmetic Ingredient Dictionary and Handbook, 12$^{th}$ Edition (2008), the disclosure of which is hereby incorporated by reference.

Suitable silicone acrylate copolymers include those comprising a poly(alkyl)acrylate backbone and a dimethicone polymer grafted to an alkyl ester side chain, such as the commercially available film former Cyclopentasiloxane (and) Acrylates/Dimethicone Copolymer (KP-545, Shin-Etsu Chemical Co., Ltd) and Methyl Trimethicone (and) Acrylates/dimethicone Copolymer (KP-549, Shin-Etsu Chemical Co., Ltd.).

Additional suitable polymeric film formers include, without limitation, Amino Bispropyl Dimethicone, Aminopropyl Dimethicone, Amodimethicone, Amodimethicone Hydroxystearate, Behenoxy Dimethicone, $C_{30-45}$ Alkyl Dimethicone, $C_{24-28}$ Alkyl Dimethicone, $C_{30-4}$5 Alkyl Methicone, Cetearyl Methicone, Cetyl Dimethicone, Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone. Particularly preferred are silicone polymers, including Methicone (as described by CTFA Monograph No. 1581, which is incorporated herein by reference), Dimethicones (as described by CTFA Monograph No. 840, which is incorporated herein by reference) and Amodimethicones as described by CTFA Monograph No. 189, which is incorporated herein by reference). In some embodiments, the film former comprises a hydrophilic film forming polymer, such as hydroxyethylcellulose or other cellulosics, PVP, and polyvinyl alcohol. Film forming polymers may be present in an amount between about 0.1% to about 15% by weight of the composition.

The compositions of the invention may also comprise a thickener, such as, for example, a polysaccharide or non-polysaccharide thickener. For example, polymers and copolymers of acrylic acid, including Acrylates Copolymer (INCI) are contemplated to be suitable. The composition may also comprise silica, xanthan gum, CMC, acrylic acid polymers, hydrated magnesium and aluminium silicates, or calcium silicates, or the like. Oil-soluble rheology modifiers such as trihydroxystearin and/or 12-hydroxystearic acid may also be included. Gellants, such as ester-terminated polyesteramides, and glutamide-based gelling agents, including N-lauroyl-L-glutamic acid dibutyl amide and N-2-ethylhexanoyl-L-glutamic acid dibutyl amide, can also be used. When present, thickeners may comprise from about 0.1% to about 15% by weight of the composition, more typically from about 1% to about 5% by weight of the composition. In some embodiments, the compositions of the invention are free of gellants or are substantially free of gellants, by which is meant that the amount of any such gellants is insufficient to provide a measurable difference in the rheology and/or gloss of said composition and in any event will be less than 0.1% by weight.

The compositions of the invention may also comprise humectants. Suitable humectants include those such as polyols (e.g., glycols), including without limitation, glycerin, $C_{3-24}$ polyols such as propylene glycol, ethoxydiglycol, butylene glycol, pentylene glycol, hexylene glycol, caprylyl glycol, sugar alcohols, sorbitol, xylitol, and the like. In one embodiment, the composition comprises Lauryl PCA in an amount from about 0.1-5% by weight. Such components may be present, for example, in an individual or collective amount between about 0.001% to about 50% by weight of the composition. In some embodiments, the compositions are free of humectants or are substantially free of humectants by which is meant that their inclusion is at levels that are insufficient to affect the gloss of the composition and/or to impart a measurable moisturizing benefit to the skin.

The compositions of the invention may include a cosmetically or dermatologically acceptable vehicle that may be substantially anhydrous. The vehicle may be in the form of, for example, a serum, a cream, a lotion, a gel, or a stick, and may comprise an emulsion (e.g., polyol-in-silicone, silicone-in-polyol emulsion, etc.), or may comprise an ethanolic vehicle, silicone (e.g., cyclomethicone, dimethicone, etc.), hydrocarbon (e.g., petrolatum, isododecane, etc.), ester oil (e.g., isopropyl myristate, myristyl myristate), or the like. The vehicle may further comprise an emulsifier, gelling agent, structuring agent, rheology modifier (e.g., a thickener), film former, or the like. The vehicle may comprise any of the oils and emollients described herein. The vehicle may comprise from about 25% to about 99% by weight of the composition.

In some embodiments, the compositions are free of or substantially free of volatile silicones, including volatile cyclomethicones, such as D4 and/or D5. In this context, "substantially free of" volatile silicones means that the compositions comprise less than 0.5% (typically, less than 0.25% or less than 0.1% by weight) volatile silicones based on the weight of the entire composition.

The compositions of the invention may also comprise one or more sunscreen actives, which may be organic or inorganic, and/or water-soluble or oil soluble, and include those with UVA and/or UVB absorbance from about 290 to about 400 nanometers solar radiation. Such sunscreen actives include, but are not limited to, one or more of the following: DEA methoxycinnamate, octylmethoxy cinnamate, drometrizole trisiloxane, oxybenzone, octyl methoxycinnamate, octyl salicylate, homomenthyl salicylate, octocrylene, avobenzone, octyl dimethyl PABA, TEA salicylate, 4-methyl benzilidene camphor, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, zinc oxide, titanium dioxide or any derivatives, or any combinations thereof. The sunscreen may be present, for example, from about 1% by weight to about 30% by weight (e.g., 5-12.5% by weight) of the total weight of the composition.

The compositions may further include an emulsifier. The amount of emulsifier will typically be from about 0.001 to about 10% by weight, but preferably will range from about 0.01 to about 5% by weight, and most preferably about 0.1 to about 1% by weight, based upon the total weight of the composition. The emulsifier may be ionic, zwitterionic, or nonionic. Suitable emulsifiers include those of the polyethoxylated type (e.g., polyoxyethylene ethers or esters), polydiorganosiloxane-polyoxyalkylene block copolymers (e.g., dimethicone copolyol), Steareth-20, Steareth-21, fatty alcohols (e.g., Cetearyl Alcohol), Polyoxethylene sorbitan fatty acid esters (i.e., polysorbates), and Hydrogenated Castor Oil, to name a few. Additional emulsifiers are provided in the INCI Ingredient Dictionary and Handbook 11th Edition 2006, the disclosure of which is hereby incorporated by reference.

The composition may comprise one or more preservatives or antimicrobial agents, such as methyl, ethyl, or propyl paraben, phenoxyethanol, BHT, and so on, in amounts ranging between about 0.0001% to about 5% by weight of the composition. In one embodiment, the preservative comprises caprylyl glycol, for example, in an amount from about 0.001-5% (or from 0.1-1%) by weight.

Other suitable components include those agents that provide a prophylactic or therapeutic benefit to skin. Particular mention may be made of alpha-hydroxy acids, beta hydroxyl acids, ascorbic acid or Vitamin C and derivatives thereof (e.g., $C_1$-$C_8$ esters thereof); retinoids such as retinol (Vitamin A) and the esters thereof (e.g., $C_1$-$C_8$ esters, such as palmitate), retinoic acid and the derivatives thereof, hyaluronic acid, chemical sun screens useful in the cosmetic field including any UVA and UVB filter useful in the cosmetic field including mixtures thereof and blends with physical filters including, but not limited to metal oxide particles such as titanium oxides and/or zinc oxides. Additional benefit agents include botanicals, thiodipropionic acid (TDPA) and esters thereof; (e.g., retinoic acid, all-trans-retinoic acid, retinaldehyde, retinol, and retinol esters such as acetates or palmitates, and others); alpha-hydroxy acids (e.g., glycolic acid), beta-hydroxy acids (e.g., salicylic acid and salicylates); exfoliating agents (e.g., glycolic acid, 3,6,9-trioxaundecanedioic acid, etc.), depigmenting agents (e.g., hydroquinone, kojic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); antioxidants (e.g., BHT, ascorbic acid, sodium ascorbate, ascorbyl palmitate, beta-carotene, thiodipropionic acid, vitamin E, etc.), barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few. These benefit agents will typically be present, if at all, in amounts between about 0.001% and about 10% by weight of the composition.

Additional ingredients may be included in the compositions, and comprise rheology modifiers, stabilizers, dispersants, active ingredients (e.g., collagenase inhibitors, elastase inhibitors, collagen stimulators, depigmenting agents, desquamating agents, etc.), preservatives, pH adjusters, colorants, fragrances, flavorants, anesthetics, anti-allergenics, antifungals, anti-inflammatories, antiseptics, chelating agents (e.g., EDTA and salts thereof), fragrances, lubricants, masking agents, medicaments, moisturizers, protectants, soothing agents, stabilizers, antioxidants (e.g., BHT, TDPA, etc.), botanicals, surfactants, viscosifiers, vitamins, or any combinations thereof. Such components may be present, for example, in an individual or collective amount between about 0.001% to about 50% by weight of the composition.

The compositions of the invention are useful for application to the human integumentary system, including, skin, lips, nails, hair, and other keratinous surfaces and keratin fibers. As used herein, the term "keratinous surface" refers to keratin-containing portions of the human integumentary system, which includes, but is not limited to, skin, lips, hair (including eyebrows and eyelashes), and nails (toenails, fingernails, cuticles, etc.) of mammalians, preferably humans. A "keratin fiber" includes hair of the scalp, eyelashes, eyebrows, facial hair, and body hair such as hair of the arms, legs, etc.

The compositions of the invention may be used in any kind of cosmetic or personal care formulation that can be applied to a human integument, and may be in the form of a solid stick, a liquid, a cream, a lotion, a powder, etc. For example, the cosmetic composition may be, without limitation, in the form of lipstick, lip color, mascara, eye liner, blush, bronzer, powder, eye shadow, nail polish, foundation, concealer, and the like. Personal care products may include, for example, day creams or lotions, night creams or lotions, sunscreen lotions, creams, or oils and other SPF products, moisturizers, salves, ointments, gels, body milks, artificial tanning compositions, depilatories, etc. In some embodiments, the compositions are in the form of a lipstick. A lipstick may have suitable hardness to be a molded, free-standing stick.

Methods are also provided for imparting matte color to the lips comprising applying the composition to the lips to form a film of lipstick composition thereon. In some embodiments, a plurality of coats is applied.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, § 201(i).

EXAMPLES

Example 1. Lipstick Compositions

Three matte lipstick compositions of the invention were prepared according to the formulas in Table 1 (A, B, and C). The three lipsticks contained identical ingredients except that Lipstick B did not include any isopropyl isostearate, and Lipstick C did not include any ethylhexyl palmitate. The formulations are presented below in Table 1.

The gloss values of lipstick compositions A, B, and C were compared to determine whether the combination of ethylhexyl palmitate and isopropyl isostearate (Lipstick A) would reduce the gloss value relative to otherwise identical lipsticks lacking either one of these ester oils (Lipsticks B and C). The shine/gloss intensity of each lipstick was assessed using a gloss test. A gloss meter determines the gloss intensity, or shine, of a cosmetic film by measuring specular reflectance. The gloss is reported in "gloss units." Films of 3 mil thickness of each lipstick were drawn onto 7 mil thick clear polyester panels. Each of the sample films was flat and free of structures. The films were allowed to dry for one hour prior to measurement. The samples were placed on a heating blanket at 35° C. to approximate the temperature of skin. A light source was placed at 20° and the specular reflection of the heated sample was measured. The results of the gloss assessment are presented in Table 1.

TABLE 1

| Ingredient | A (Wt. %) | B (Wt. %) | C (Wt. %) |
|---|---|---|---|
| Dimethicone/Dimethicone Crosspolymer (80/20) (emollient) | 17.5 | 17.5 | 17.5 |
| Ethylhexyl Palmitate (ester oil) | 17.01 | 26.89 | — |
| Isopropyl Isostearate (ester oil) | 9.88 | — | 26.89 |
| Microcrystalline (wax) | 1.4 | 1.4 | 1.4 |
| Paraffin (wax) | 2.4 | 2.4 | 2.4 |
| Carnauba (wax) | 0.3 | 0.3 | 0.3 |
| Ozokerite (wax) | 5 | 5 | 5 |
| Polyethylene-Linear (wax) | 5.3 | 5.3 | 5.3 |
| Lanolin (emollient) | 4 | 4 | 4 |
| Polyglycerol Diisostearate (emollient) | 3.5 | 3.5 | 3.5 |
| C18-38 Alkyl Hydroxystearoyl Stearate | 0.5 | 0.5 | 0.5 |

TABLE 1-continued

| Ingredient | A (Wt. %) | B (Wt. %) | C (Wt. %) |
|---|---|---|---|
| (emollient) | | | |
| Tocopheryl Acetate (emollient) | 0.05 | 0.05 | 0.05 |
| Ethylhexyl-Methoxycinnamate (sunscreen) | 7.5 | 7.5 | 7.5 |
| Calcium Silicate-Hydrous (powder) | 2.74 | 2.74 | 2.74 |
| Silica-Spherical (~2-20 Microns) (powder) | 2.4 | 2.4 | 2.4 |
| Polyethylene (~12 Micron) (powder) | 5 | 5 | 5 |
| Polymethylsilsesquioxane (powder) | 2.7 | 2.7 | 2.7 |
| Iron Oxide (pigment) | 0.186 | 0.186 | 0.186 |
| D&C Red No. 7 (lake) | 6.37 | 6.37 | 6.37 |
| D&C Red No. 6 (lake) | 3.69 | 3.69 | 3.69 |
| FD&C Yellow No. 5 (lake) | 0.735 | 0.735 | 0.735 |
| Mica (powder) | 0.019 | 0.019 | 0.019 |
| Lauryl PCA (humectant) | 1 | 1 | 1 |
| Acrylate Copolymer (thickener) | 0.135 | 0.135 | 0.135 |
| Fragrance | 0.135 | 0.135 | 0.135 |
| Butylated Hydroxytoluene (preservative) | 0.05 | 0.05 | 0.05 |
| Caprylyl Glycol (preservative) | 0.5 | 0.5 | 0.5 |
| Gloss Value | 5.17 (±0.94) | 8.08 (±1.30) | 8.01 (±1.75) |

The gloss value of Lipstick B (lacking isopropyl isostearate) was 8.08±1.30, and the gloss value of Lipstick C (lacking ethylhexyl palmitate) was 8.01±1.75. Lipstick A, which contained both isopropyl isostearate and ethylhexyl palmitate, gave a substantially reduced gloss value of 5.17±0.94 gloss units, indicating that Lipstick A is characterized by a lower shine or gloss, and therefore a more matte finish relative to Lipsticks B and C. In addition, Lipstick A shows a synergistic reduction in gloss value compared to Lipsticks B or C.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. A matte lipstick comprising ethylhexyl palmitate and isopropyl isostearate, wherein the weight ratio of said ethylhexyl palmitate to said isopropyl isostearate is from about 1.72:1 to about 2:1.

2. The matte lipstick according to claim 1, further comprising from about 5% to about 20% by weight non-volatile dimethicone oil and from about 1% to about 10% by weight silicone crosspolymer.

3. The matte lipstick according to claim 1, wherein the gloss value of said composition is less than 7.

4. The matte lipstick according to claim 1, comprising one or more additional emollients, wherein the aggregate amount of all emollients is between about 40% to about 60% by weight.

5. The matte lipstick according to claim 4, wherein said additional emollients comprise non-volatile dimethicone oil, polyglycerol diisostearate, or silicone crosspolymers.

6. The matte lipstick according to claim 1, comprising one or more additional ester oils and one or more waxes, wherein the aggregate weight of all ester oils is greater than the aggregate weight of all waxes.

7. The matte lipstick according to claim 6, wherein the aggregate weight all ester oils is between about 10% and about 40% by weight.

8. The matte lipstick according to claim 7, wherein said waxes are present in amount between about 5% and about 20% by weight.

9. The matte lipstick according to claim 8, wherein said waxes comprise paraffin wax, ozokerite wax, and microcrystalline wax.

10. The matte lipstick according to claim 1 comprising from about 1% to about 10% by weight of a silicone crosspolymer.

11. The matte lipstick according to claim 1, further comprising spherical silica, calcium silicate, and polyethylene powder.

12. A method of imparting matte color to a human integument comprising applying to the human integument a film of a composition according to claim 1.

13. A method of imparting matte color to a human integument comprising applying to the human integument a film of a matte lipstick comprising:
   (a) from about 10% to about 30% by weight ethylhexyl palmitate and between about 1% and about 20% by weight isopropyl isostearate, wherein the ratio of ethylhexyl palmitate to isopropyl isostearate is from about 1.72:1 to about 2:1;
   (b) from about 1% to about 10% by weight of a silicone crosspolymer;
   (c) from about 1% to about 20% by weight of a mattifying powder comprising calcium silicate, spherical silica, and polyethylene powder; and
   (d) from about 1% to about 25% by weight of one or more colorants;
wherein said film is characterized by a gloss value of less than 10.

14. The method according to claim 13, wherein said ethylhexyl palmitate comprises from about 15% to about 25% by weight of the composition; said isopropyl isostearate comprises from about 5% to about 15% by weight of the composition.

15. The composition according to claim 1, wherein said composition comprises:
   (a) from about 10% to about 30% by weight ethylhexyl palmitate and between about 5% and about 15% by weight isopropyl isostearate;
   (b) from about 1% to about 10% by weight of a silicone crosspolymer;
   (c) from about 1% to about 20% by weight of a mattifying powder comprising calcium silicate, spherical silica, and polyethylene powder; and
   (d) from about 1% to about 25% by weight of one or more colorants.

16. The composition according to claim 1, wherein said composition comprises between about 1% and about 10% polyethylene powder by weight of the composition.

* * * * *